United States Patent
Rulkens et al.

(10) Patent No.: US 10,233,287 B2
(45) Date of Patent: Mar. 19, 2019

(54) PROCESS FOR THE PREPARATION OF DIAMINE/DICARBOXYLIC ACID SALTS AND POLYAMIDES THEREOF

(71) Applicant: DSM IP ASSETS B.V., Heerlen (NL)

(72) Inventors: Rudy Rulkens, Echt (NL); Renier Henricus Maria Kierkels, Echt (NL); Geert Adelina Rudolf Vanden Poel, Echt (NL); Theo Joseph Cuypers, Echt (NL); Eric Grolman, Echt (NL)

(73) Assignee: DSM IP ASSETS B.V., Heerlen (NL)

(*) Notice: Subject to any disclaimer, the term of this patent is extended or adjusted under 35 U.S.C. 154(b) by 289 days.

(21) Appl. No.: 14/763,617

(22) PCT Filed: Jan. 30, 2014

(86) PCT No.: PCT/EP2014/051803
§ 371 (c)(1),
(2) Date: Jul. 27, 2015

(87) PCT Pub. No.: WO2014/118277
PCT Pub. Date: Aug. 7, 2014

(65) Prior Publication Data
US 2015/0353682 A1    Dec. 10, 2015

(30) Foreign Application Priority Data

Jan. 31, 2013 (WO) .................. PCT/EP2013/051972

(51) Int. Cl.
| | |
|---|---|
| C08G 69/32 | (2006.01) |
| C07C 51/41 | (2006.01) |
| C07C 209/68 | (2006.01) |
| C08G 69/26 | (2006.01) |
| C07C 211/09 | (2006.01) |
| C07C 211/12 | (2006.01) |
| C08G 69/28 | (2006.01) |

(52) U.S. Cl.
CPC .............. *C08G 69/32* (2013.01); *C07C 51/41* (2013.01); *C07C 51/412* (2013.01); *C07C 209/68* (2013.01); *C07C 211/09* (2013.01); *C07C 211/12* (2013.01); *C08G 69/26* (2013.01); *C08G 69/265* (2013.01); *C08G 69/28* (2013.01)

(58) Field of Classification Search
None
See application file for complete search history.

(56) References Cited

U.S. PATENT DOCUMENTS

| | | | |
|---|---|---|---|
| 3,379,696 | A | 4/1968 | Fritz |
| 5,801,278 | A | 9/1998 | Bletsos et al. |
| 2006/0122360 | A1 | 6/2006 | Tsujii et al. |
| 2009/0127117 | A1 | 5/2009 | Miura et al. |
| 2012/0245308 | A1 | 9/2012 | El-Toufaili et al. |
| 2013/0172521 | A1 | 7/2013 | Nakai et al. |
| 2013/0338333 | A1 | 12/2013 | Nakai et al. |

FOREIGN PATENT DOCUMENTS

| | | |
|---|---|---|
| JP | 2001-513820 | 9/2001 |
| WO | 2012/070457 | 5/2012 |
| WO | 2012/118107 | 9/2012 |

OTHER PUBLICATIONS

International Search Report for PCT/EP2014/051803, dated Apr. 14, 2014, 3 pages.

*Primary Examiner* — Rachel Kahn
(74) *Attorney, Agent, or Firm* — Nixon & Vanderhye P.C.

(57) ABSTRACT

The invention relates to a process for preparing a salt from diamine and dicarboxylic acid, the process comprising contacting a diamine gas, having a gas temperature T-gas, with a dicarboxylic acid, thereby forming a reaction mixture comprising diamine/dicarboxylic acid salt, wherein the dicarboxylic acid and the reaction mixture are kept at a temperature T-mixture of at least 10° C. below the lowest of the melting temperature of the dicarboxylic acid (Tm-acid) and the melting temperature of the resulting diamine/dicarboxylic acid salt (Tm-salt). The invention also relates to a process for preparing a polyamide comprising preparing a salt from diamine and dicarboxylic acid.

25 Claims, No Drawings

PROCESS FOR THE PREPARATION OF DIAMINE/DICARBOXYLIC ACID SALTS AND POLYAMIDES THEREOF

This application is the U.S. national phase of International Application No. PCT/EP2014/051803 filed 30 Jan. 2014 which designated the U.S. and claims priority to International Application No. PCT/EP2013/051972 filed 31 Jan. 2013, the entire contents of each of which are hereby incorporated by reference.

The invention relates to a process for preparing a salt from diamine and dicarboxylic acid, the salt being referred to as and diamine/dicarboxylic acid salt, and abbreviated as DD-salt. The invention also relates to a process for preparing polyamides made from diamine and dicarboxylic acid, so called AA-BB polyamides, and more particular to a process for preparing semi-crystalline AA-BB polyamides.

There are various ways to produce a polyamide. Polyamides prepared from diamine and dicarboxylic acid are often manufactured by condensing appropriate salts of the diamine and dicarboxylic acid. The known processes include melt polymerization, solution polymerization, suspension polymerization, and solid-state polymerization, and combinations thereof. Salts used in such processes are generally prepared in solution or suspensions, mostly from aqueous solutions.

The first aim of the present invention is to provide a new process for preparing a salt from diamine and dicarboxylic acid. A second aim is to provide an optimized process for preparing a semi-crystalline semi-aromatic polyamide from diamine and dicarboxylic acid.

The first aim has been achieved by the process according to the invention, comprising contacting a diamine gas, having a gas temperature T-gas, with a dicarboxylic acid, thereby forming a reaction mixture comprising diamine/dicarboxylic acid salt, wherein the dicarboxylic acid and the reaction mixture are kept at a temperature T-mixture of at least 10° C. below the lowest of the melting temperature of the dicarboxylic acid (Tm-acid) and the melting temperature of the resulting diamine/dicarboxylic acid salt (Tm-salt).

A direct result of the process according to the invention is that no reaction media wherein reactants are dissolved or dispersed are used, and thus there is no need to isolate and recover the salt from such media. Surprisingly, the reaction is fast and leads to high conversion. The reaction is a solid/gas reaction, due the fact that the diamine is provided as a gas; however the reaction mixture remains in the solid state, which allows for obtaining the salt as discrete solid particles. Contacting the diamine as a gas with the dicarboxylic acid reduces the risk of excessive wetting and sticking of particles and results in an effective distribution of diamine over dicarboxylic acid particles.

With the term melting temperature (Tm), as used herein, unless expressed otherwise, is herein understood the peak temperature of the endothermic melting peak in the first heating cycle measured by DSC by the method according to ISO 11357-1/3 (2009) with a scan rate of 20° C./min.

The dicarboxylic acid is suitably provided as a powder, as granules of granulated powder or as pellets of compressed powder, or as a mixture thereof.

A powder is herein understood to be granular material consisting of discrete and substantially solid particles. These particles, referred to as powder particles, suitably have a particle size of from sub-micron to about 2 mm or less.

Granules and pellets will typically be of larger size than the powder particles, as each of these granules and pellets will comprise multiple powder particles. Suitably, the granules will have a particle size of from sub-millimeter to centimeter scale, generally from about 0.5 mm to 4 cm, for example from about 2 mm to about 2 cm. Suitably, the pellets will have a main diameter of a few millimeters, for example from about 1 to 8 mm, such about 2-5 mm. Suitably, the pellets will have a particle size of from millimeter to centimeter scale, generally from about 1 mm to 1 cm, for example from about 2 mm to about 5 mm.

The process is suitably carried out at ambient pressure, but may also be carried out at lower or higher pressure. Preferably, the contacting is carried out under an absolute pressure of at most 5 bar, preferably at most 3 bar, more preferred at most 1 bar. The lower pressure leads to lower temperatures to convert diamine into a diamine gas, which is in particular favourable for using higher boiling diamines, and for reducing or avoiding diamine degradation.

In the process according to the invention the temperature of the dicarboxylic acid and that of the reaction mixture is preferably at least 20° C. below the lowest of Tm-acid and Tm-salt, more preferred at least 20° C. below the lowest of Tm-acid and Tm-salt. A lower T-mixture contributes to better retention of the reaction mixture in solid state and reduces risk of sticking of particles.

In a particular embodiment of the invention, T-gas is at least 5° C. above T-mixture. The advantage is that the diamine gas is more effectively absorbed by the dicarboxylic acid and converted into the salt.

The process according to the invention is suitably carried out in an agitated bed reactor. An agitated bed reactor is preferably applied when T-gas is at least 5° C. above T-mixture. This further reduces the change for local excessive wetting and reduces sticking of particles. In an agitated reactor the carboxylic acid and the subsequent reaction mixture are converted into an agitated bed. Preferably, the diamine gas is led into the agitated bed. This limits or prevents condensation on cold spots, and contributes to the preparation of a flowable salt. For the agitated bed reactor suitably a rotating vessel or a mechanically stirred reactor is used.

In another embodiment T-gas is below T-mixture plus 5° C., preferably T-gas is equal to or below T-mixture. A lower T-gas has the advantage that the risk for fouling and condensation of diamine gas on cold spots is avoided.

T-gas equal to T-mixture can be accomplished, for example, by heating the diamine and the dicarboxylic acid in one reactor at the same temperature. T-gas below T-mixture can be accomplished, for example, by providing the diamine gas at T-gas from outside into a reactor comprising the dicarboxylic acid at T-mixture.

In the process according to the invention wherein T-gas is below T-mixture plus 5° C., and preferably equal to or below T-mixture, the contacting may be carried out in a static bed reactor or a moving bed reactor. In such reactors the carboxylic acid and the subsequent reaction mixture constitute a static bed, respectively a moving bed. The advantage is that attrition of particles in the reaction mixture, if any, is further reduced. The static bed reactor can be, for example, a batch wise operated vertical column reactor. For the moving bed reactor, for example, a continuously operated vertical column reactor can be used. In both static as well as moving bed reactor, the diamine gas can be led through the bed, thereby being used even more effectively for the salt formation. The diamine may be conveyed by means of a carrier gas, suitably an inert gas, such as nitrogen. Suitably, the gas is supplied in a continuous flow, suitably in a closed loop.

The diamine gas is suitably prepared by heating a diamine to its boiling temperature at the given pressure, or leading a carrier gas through liquid diamine.

For the preparation of the salt different diamines and dicarboxylic acids can be used.

Suitably, the dicarboxylic acid comprises an aliphatic dicarboxylic acid, or an aromatic dicarboxylic acid, or a mixture thereof.

The dicarboxylic acid suitably comprises a mixture two or more dicarboxylic acids, for example a mixture of an aliphatic dicarboxylic acid and aromatic dicarboxylic acid. In these cases the salt-preparation will result in a mixture of salts, as can generally be confirmed by observation of different melting temperatures of the salts in DSC measurements. In the case of a mixture, wherein the dicarboxylic acid shows two or more melting peaks, Tm-acid is considered to be the melting temperature corresponding with the peak at the lowest melting temperature. Analogously, where the resulting diamine/dicarboxylic acid salt shows two or more melting peaks, Tm-salt is considered to be the melting temperature corresponding with the peak at the lowest melting temperature. T-mixture shall be kept at least 10° C. below the lowest of the melting temperatures.

Suitably the aliphatic dicarboxylic acid is an aliphatic dicarboxylic acid having 4-8 carbon atoms, and preferably chosen from the group of 1,4-butanedioic acid (also known as succinic acid), 1,6-hexanedioic acid (also known as adipic acid), 1,8-octanedioic acid (also known as suberic acid) and trans-1,4-cyclohexanedicarboxylic acid. More preferred, the aliphatic dicarboxylic acid consists of adipic acid, or trans-1,4-cyclohexanedicarboxylic acid, or a combination thereof. Adipic acid is the most widely used aliphatic dicarboxylic acid in semi-crystalline polyamides, whereas trans-1,4-cyclohexanedicarboxylic acid gives DD-salts with a higher melting point and can be used for preparing semi-crystalline polyamides with higher melting points.

The aromatic dicarboxylic acid may comprise, for example isophthalic acid, terephthalic acid, 2,6-naphthalene dicarboxylic acid and biphenyl-4,4'-dicarboxylic acid. Preferably, the aromatic dicarboxylic acid is selected from terephthalic acid, 2,6-naphthalene dicarboxylic acid and biphenyl-4,4'-dicarboxylic acid, or a combination thereof. Terephthalic is herein most preferred, as it mostly used in semi-crystalline semi-aromatic polyamides.

In a particular embodiment, the dicarboxylic acid comprises at least 50 mole %, of an aromatic dicarboxylic acid selected from terephthalic acid, 2,6-naphthalene dicarboxylic acid and biphenyl-4,4'-dicarboxylic acid, or a combination thereof, and optionally (b) at most 50 mole % of an aliphatic dicarboxylic acid, selected from adipic acid and cyclohexane dicarboxylic acid, or a combination thereof; and (c) at most 10 mole % of another dicarboxylic acid. Herein the mole percentage (mole %) are relative to the total molar amount of dicarboxylic acid. This embodiment allows for the preparation of a DD-salt, which is favourably being used in a direct solid-state polymerization process as described further below.

More preferred, the dicarboxylic acid comprises at least 90 mole %, and even better for at least 95 mole %, of an aromatic dicarboxylic acid selected from terephthalic acid, 2,6-naphthalene dicarboxylic acid and biphenyl-4,4'-dicarboxylic acid, or a combination thereof. The advantage hereof is that these acids, as well as the salts resulting thereof have higher melting temperatures than, for example, adipic acid and isophthalic acid, thereby allowing higher temperatures for T-mixture, leading to faster reaction and thereby resulting in shorter reaction times. This is in particular favourable for performing the process in a static bed reactor or moving bed reactor, wherein T-gas is below T-mixture plus 5° C. Suitably, T-mixture is kept herein below 210° C.

The diamine used in the process according to the invention is suitably selected from aliphatic diamines and aliphatic-aromatic diamines, or a combination thereof. Aliphatic-aromatic diamines herein understood to be diamines wherein each of the amine groups are directly connected to an aliphatic moiety, and which aliphatic moieties in turn are connected to an aromatic moiety.

The aliphatic diamine suitably comprises a C2-C12 diamine, i.e. a diamine having from 2 to 12 carbon atoms. Herein, using shorter chain diamines favours the formation of a diamine gas, due to lower boiling temperatures. The aliphatic diamine may comprise a linear aliphatic diamine, a branched aliphatic diamine or a cyclo-aliphatic diamine, or a combination thereof.

More particularly, the C2-C12 aliphatic diamine is a linear aliphatic diamine selected from 1,2-ethylenediamine, 1,3-propanediamine, 1,4-butanediamine, 1,5-pentanediamine, 1,6-hexanediamine, and 1,4-cyclohexanediamine, which are examples of C2-C6 diamines; and 1,7-heptane diamine, 1,8-octanediamine, 1,9-nonanediamine, 1,10-decanediamine, and 1,12-dodecane-diamine, which are examples of C7-C12 diamines.

Preferably, the diamine comprises a linear C2-C10 diamine, or trans-1,4- cyclohexanediamine, or a combination thereof. This leads to a DD-salt with a higher melting point. Suitably, the diamine comprises at least 50 mole % of said diamine, preferably at least 75 mole %, and even more preferred consists of said diamine. Herein the mole % is relative to the total molar amount of diamine contacted with the dicarboxylic acid.

In preferred embodiment, wherein the dicarboxylic acid comprises an aliphatic dicarboxylic acid, the diamine comprises a C2-C6 diamine selected from 1,2-ethylenediamine, 1,3-propanediamine, 1,4-butanediamine, 1,5-pentanediamine, and 1,6-hexanediamine, and trans-1,4-cyclohexanediamine, or a combination thereof. The advantage is that the diamine has a lower boiling point and the resulting salt has a higher melting temperature. Suitably, the diamine comprises at least 50 mole % of said diamine, preferably at least 75 mole %, and even more preferred consists of said diamine. Herein the mole % is relative to the total molar amount of diamine contacted with the dicarboxylic acid.

As indicated above the diamine may comprise a mixture of different diamines. This has the advantage that the boiling temperature is lower, which favours the formation of the diamine gas. The relative amounts of the diamines contacted with the dicarboxylic acid can be steered by steering the composition of the diamine in the mixture and can be determined by analysis of the resulting salt. Analysis can be done, for example by dissolving the salt in deuterated water (D2O) and performing proton-NMR.

Suitably, the diamine is added in such an amount that the diamine/dicarboxylic acid molar ratio in the DD-salt obtained from the process is in the range of 0.90-1.10.

The DD-salt obtained by the process according to the invention, i.e. the diamine/dicarboxylic acid salt, is suitably used for the preparation of polyamides.

The invention is also directed to an optimized process for preparing polyamides. This process concerns preparing a semi-crystalline polyamide from diamine and dicarboxylic acid, and comprises (i) contacting a diamine gas, having a gas temperature T-gas, with a dicarboxylic acid, thereby forming a reaction mixture comprising the dicarboxylic acid and diamine/dicarboxylic acid salt, wherein the dicarboxylic acid and the reaction mixture are kept at a temperature T-mixture of at least 10° C. below the lowest of the melting temperature of the dicarboxylic acid (Tm-acid) and the melting temperature of the resulting diamine/dicarboxylic acid salt (Tm-salt)

(ii) solid-state polymerizing the DD-salt, thereby obtaining the polyamide.

Solid-state polymerization of diamine/dicarboxylic acid salts is known in the art. However not with salts prepared by contacting a diamine gas with a dicarboxylic acid as in step (i). It is not only surprising that the salt preparation can be done as according to step (i). Another direct result of the process according to the invention is that all steps are done in the solid state, thus without melting, or dissolving or dispersing in a liquid, or cooling with a cryogenic medium, or alike. Use of solvents, dispersing agents, cryogenic media, and handling and recycling thereof can be omitted, thereby saving on handling and energy costs.

With the term solid-state polymerization is herein understood that the polymerization is carried out under conditions such that the DD-salt, the polyamide and any intermediate condensation product thereof remain in the solid state. This is accomplished by using reaction temperatures for the condensation step(s) below the melting temperature of the DD-salt, respectively below the melting temperature of the polyamide, and any intermediate product thereof. The process can be carried out in different steps, wherein initially the condensation temperature is kept below the melting temperature of the DD-salt, and after a prepolymer is formed below the melting temperature of the prepolymer and the melting temperature of the polyamide. Suitably, the condensation temperature is kept at least 10° C., preferably at least 20° C. below melting temperature of the salt, respectively at least 15° C., preferably at least 25° C. below melting temperature of the prepolymer and the polyamide.

Polyamides made from diamine and dicarboxylic acid are also known as AA-BB polyamides. The nomenclature is adhered to as used in Nylon Plastics Handbook, Edited by Melvin I. Kohan, Hanser Publishers, 1995; e.g. PA-6T denotes a homopolymer with building blocks 1,6-hexanediamine and terephthalic acid, PA-66/6T denotes a copolymer made from 1,6-hexanediamine, adipic acid and terephthalic acid and a blend of PA-66 and PA-6T is described as PA-66/PA-6T.

The term "polyamide" as used herein includes both homopolyamides and copolyamides, unless specifically expressed otherwise. The process according to the invention allows for the production of a copolyamide, or polyamide copolymer, when more than one diamine and/or more than one dicarboxylic acid are used, whereas a homopolyamide, or polyamide homopolymer, is produced when only one diamine and one dicarboxylic acid are used. Homopolyamides and copolyamides are herein together also referred to as (co)polyamide.

With the terms "diamine" and "dicarboxylic acid" in the wording "the polyamide is prepared from diamine and dicarboxylic acid" is also meant to include diamine comprising two or more different diamines, as well as dicarboxylic acid comprising two or more different dicarboxylic acids, unless explicitly or implicitly indicated otherwise. For example for homopolyamides only one diamine and only one dicarboxylic acid are used.

The semi-crystalline polyamide prepared by the process can be a semi-crystalline aliphatic polyamide, as well as a semi-crystalline semi-aromatic polyamide. In this process step (i) is suitably carried out as described as above for the salt preparation and any preferred or special embodiments thereof.

Examples of suitable aliphatic polyamides include PA-46 and PA-66.

In a preferred embodiment of the process according to the invention, the semi-crystalline polyamide is a semi-crystalline semi-aromatic polyamide, wherein
  the diamine comprises at 90 mole %, relative to the total molar amount of diamine, of a linear aliphatic C2-C10 diamine or an aliphatic-aromatic diamine, wherein or a mixture thereof
  the dicarboxylic acid comprises at least 50 mole %, relative to the total molar amount of dicarboxylic acid, of an aromatic dicarboxylic acid selected from terephthalic acid, 2,6-naphthalene dicarboxylic acid and biphenyl-4,4'-dicarboxylic acid, or a combination thereof.

Herein T-mixture in step (i) is suitably below 210° C.; the solid state polymerisation (step (ii) is at least partly carried out at a temperature above 220° C. The semi-crystalline semi-aromatic polyamide so produced is obtained in high yield in a relative short reaction time.

Examples of suitable copolyamides that can be prepared with this preferred embodiment include copolymers of PA-XT with PA-X6 or PA-XCHDA, wherein X comprises a C4-C6 diamine, or a combination thereof. For example PA-4T/46, PA-4T/4CHDA, PA-6T/66, PA-6T/6CHDA and PA4T/DACH6. Herein CHDA represents repeat units derived trans-1,4-cyclohexanedicarboxylic acid and DACH refers to trans-1,4-diaminocyclohexane.

In a special embodiment, the dicarboxylic acid consists for at least 95 mole %, relative to the total molar amount of dicarboxylic acid, of an aromatic dicarboxylic acid selected from terephthalic acid, 2,6-naphthalene dicarboxylic acid and biphenyl-4,4'-dicarboxylic acid. The advantage hereof is that the condensation can be carried out at higher temperatures thereby obtaining the polyamide in even shorter reaction times.

The salt preparation step (i) and solid-state condensation step (ii) may be carried out as separate steps, but alternatively also as overlapping steps.

The special embodiment may be carried out such that in step (i) T-mixture is below 210° C. and in step (i) the diamine is added in an amount such that the diamine/dicarboxylic acid molar ratio in the DD-salt obtained from step (i) is in the range of 0.75-1.10. It has been observed that excess of diamine is easily stripped off before or during the solid-state step (ii); whereas deficiency can be compensated during step (ii) by supplemental addition of diamine, e.g. with diamine gas.

In another special embodiment, T-mixture in step (i) may be above 210° C., even above 220° C. The advantage thereof is that the solid-state condensation already takes place along with the salt formation, thereby resulting in even shorter polymerization times.

Examples of suitable homopolyamides that can be prepared with the this special embodiment include PA-2T, PA-3T, PA-4T, PA-5T, PA-6T, PA-7T, PA-8T, PA-9T and PA-10T.

Examples of suitable copolyamides that can be prepared with the this special embodiment include copolymers of PA-2T, PA-3T, PA-4T, PA-5T, PA-6T, such as PA-4T/XT, PA-6T/XT, e.g. PA-4T/6T, PA-6T/5T, PA-4T/10T, PA-6T/10T, PA-6T/4T/10T, PA-6T/9T, PA-6T/7T, PA-4T/8T, PA-4T/6T/10T and PA-4T/10T, PA-6T/8T, PA-4T/DACHT where DACH refers to trans-1,4-diaminocyclohexane and corresponding copolyamides wherein terephthalic acid (T) is substituted by 2,6-naphthalene dicarboxylic acid or biphenyl-4,4'-dicarboxylic acid. Herein 4 represents repeat units derived from 1,4-butanediamine, 5 represents repeat units derived from 1,5-pentanediamine, 6 represents repeat units derived from 1,6-hexanediamine, 7 represents repeat units derived from 1,7-heptane diamine, 8 represents repeat units derived from 1,8-octanediamine, 10 represents repeat units derived from 1,10-decanediamine.

The solid-state polymerization step (ii) may be carried out in any reactor that is suitable for direct solid-state polymerization of DD-salt. Step (ii) is suitably carried out in a static bed reactor, a moving bed reactor, or an agitated bed reactor. Suitably, the solid-state polymerization step is carried out in the same reactor as wherein the salt-preparation is done.

The invention is further illustrated with the following non-limiting examples.
Raw materials
Terephthalic acid: powder, industrial grade, melting temperature above 400° C.; Powder with particle size d10 36 um, d50 127 um, d90 264 um
1,10-Diaminodecane: industrial grade; max 1 wt. % water, impurities in ppm range; melting temperature 62° C.
Hexamethylene diamine: (HMDA) industrial grade max 1 wt. % water, impurities in ppm range; melting temperature 41° C. Boiling temperature at 1 bara: 205° C.
Diaminobutane (DAB), Industrial grade, Boiling temperature at 1 bara: 158° C.

EXAMPLE I

The salt was prepared in a 2 liter autoclave reactor provided with wall and top heating. 25.56 g (0.22 mol) 1,6-hexane diamine was charged at the bottom of the reactor. 33.22 g (0.2 mol) terephthalic acid powder was charged to a tray, mounted in the reactor above the 1,6-hexane diamine, thereby avoiding direct contact between the terephthalic acid and the 1,6-hexane diamine. The reactor was inertized by flushing with nitrogen gas. The reactor was closed and the reactor temperature was raised with a heating rate of 1° C./min to 205° C. After 2 hours at 205° C., the heating of the reactor was turned off and the reactor was left to cooling to room temperature while providing a nitrogen flush stream of 5 liters per hour to remove the excess diamine. The product in the tray was discharged from the reactor. The product was a white powder. The results for the analytical characterization of the powder are the following: end-group content: NH2 6.98 meq/g; CO2H 7.12 meq/g; DSC results: Tm=283° C.; ΔHm=435 J/g.

The diamine/dicarboxylic acid molar ratio is 0.98. The melting temperature corresponds with that of the salt of 1,6-hexane diamine and terephthalic acid powder. The end-group content is close to that of the pure salt, which has a theoretical end-group content of 7.08 meq/g for both the NH2 and CO2H end-groups.

EXAMPLE II

Polymerization of Salt from Example I

The experiment was performed in a Mettler-Toledo TGA/DSC instrument. Approximately 7.56 mg of the salt of Experiment I was weighed with a precision balance and encapsulated in (crimped) 40 μl aluminium crucible. The aluminium crucible was sealed with a perforated aluminium crucible lid with a hole diameter of 0.05 mm. An identical empty crucible was used as a reference. Nitrogen was purged at a rate of 50 ml/min. Heating occurred with a rate of 1° C./min from room temperature to 260° C., followed by an isothermal period of 2 hours and cooled to room temperature in 30 minutes. The polymer was obtained as a powder. The resulting polyamide showed a melting point by DSC of 341° C.

EXAMPLE III

Combined Salt Formation and Polymerization of 1,10-Decanediamine with Terephthalic The experiment was performed in a 2 liter autoclave reactor provided with wall and top heating and a nitrogen gas inlet. 33.55 g (0.195 mol) 1,10-decane diamine was charged at the bottom of the reactor. 29.45 g (0.177 mol) terephthalic acid powder was charged to a tray, mounted in the reactor above the 1,10-decane diamine, thereby avoiding direct contact between the terephthalic acid and the 1,10-decane diamine. The reactor was inertized by flushing with nitrogen gas. The reactor was closed and the reactor temperature was raised with a heating rate of 1° C./min to 230° C. After 2 hours at 230° C., the reactor content was cooled to room temperature in two hours while providing a nitrogen flush stream of 5 liters per hour to remove the excess diamine. The product in the tray was discharged from the reactor. The product was a white powder. Analytical characterization by DSC: Tm=276° C. with shoulder from 290 to 316° C. showing polymer formation; ΔHm=290 J/g.

The following examples were carried out in a static bed reactor with a set-up as described below.
Static Bed Reactor.

For the reactions with a static bed a reactor with a gross volume of about 1.0 liters, comprising a heating mantle, a closing lid, a round bottom glass container and a glass wall reaction vessel was used. The glass wall reaction vessel had a diameter of about 10,5 centimeter and a height of about 14 cm. The bottom of the glass wall reaction vessel consisted of a layer of sintered glass. The sintered glass layer was provided with a drilled hole with a diameter of 1 cm. A glass tube with outer diameter of about one centimeter and a length of about 6 cm was fitted with one end in the hole. The glass container had an inner diameter of about 11 cm, so slightly larger than the reaction vessel with an inner ring at about 6 cm above the bottom of the container. The round bottom glass container was positioned in the heating mantle, and glass wall reaction vessel was positioned in the container in sealing alignment of the vessel with the inner ring. The closing lid was provided with a metal feeding tube, a feed container with a Gilson dosing pump connected to the feeding tube, a pressure gauge, a PT 100 thermometer and a gas inlet/outlet tube with an electronic valve and a gas feeding unit. The metal feeding tube was positioned such as to protrude through the small glass tube into the space of the glass container, close to the bottom of the glass container and sealed from the reaction vessel, while the PT 100 thermometer protruded into the glass wall reaction vessel, when closing the lid. The described positioning of the metal feeding tube allowed introducing the diamine in liquid form into the bottom part of the reactor without contacting the dicarboxylic acid powder, and to heat and vaporize the liquid diamine and uniformly spread over the reactor volume and contact the dicarboxylic acid powder in gaseous form. The reactor vessel was loaded with glass beads of about 5 millimeter in diameter up to a height of about 8 centimeters below the open end of the vessel(top).

EXAMPLE IV 15 grams of diaminobutane was charged to the feed container and heated to a temperature of 60° C. 26 grams of terephthalic acid powder was charged in the reaction vessel, evenly distributing over the top layer of glass beads, without exerting any mechanical force. The powder distributed over the glass beads and into the interstitial spaces between the beads. The reactor was closed with the lid, inertized with nitrogen by repeating the cycle of introducing nitrogen gas and releasing the gas, and after the last time the gas was released the valve was closed. The pressure in the reactor was 1 bar. The reactor wall and lid were electrically heated to a temperature of 160° C. The temperature of the reactor content raised to 160° C. in about the same time. Once the temperature of the reactor content reached 160° C., the overpressure in the reactor was released by shortly opening the valve, and closing it again afterwards. Then the dosing of the diamine was started. The diamine was dosed in 30 minutes. During the dosing the pressure increased to about 0.8 bar overpressure and during about 30 minutes after the dosing the pressure further increased to about 1.7 bar overpressure, and then gradually decreased over time. The temperature of the reactor content remained 160° C. The reactor was left for 30 hours, calculated from the start of the dosing, at 160° C. Then the reactor was cooled to room temperature, the reaction vessel was taken out and the reactor content was poured into a sieve. The glass beads remained on the sieve and the product powder passed through the sieve and was collected. The product powder was further analyzed and part of it was used for polymerization.

EXAMPLE V

Example IV was repeated, except that the reactor was closed at an nitrogen gas overpressure of about 0.8 bar and that the total reaction time, calculated from the start of the dosing, was reduced to 15 hours. During the dosing and the period shortly after the overpressure increased similarly to Example I, thereby resulting in a total overpressure of about 2.5 bar. The resulting product powder was collected and further analyzed in the same way as for Example I. Also part of it was used for polymerization.

EXAMPLE VI

Example IV was repeated, except that the diamine used consisted of a mixture of 5 g butane diamine and 11.5 g hexane diamine was charged to 24 grams of terephthalic acid powder in the reaction vessel. During the dosing and the period shortly after the overpressure increased similarly to Example I. The resulting product powder was collected and further analyzed in the same way as for Example I. Also part of it was used for polymerization.
Direct Solid State Polymerization.

The salts obtained in Examples IV-VI were subjected to direct solid state polymerization step in a small polymerization reactor, wherein the salts were heated in three hours to 260° C., kept for three hours at 260° C. and then cooled to room temperature. The weight loss and the resulting melting temperature of the polyamide was measured.

Comparative Experiments

Similar direct solid state polymerization experiments were carried out with salts obtained via a conventional route for reference purposes. The results for references 1 and 2 are also shown in
The results for Examples IV-VI and References 1 and 2 are shown in Table 1.

TABLE 1

| Results | | | | | |
|---|---|---|---|---|---|
| | EX-IV | EX-V | EX-VI | Ref. 1 | Ref. 2 |
| TPA molar amount | 0.157 | 0.157 | 0.147 | 4T salt | 4T/6T salt |
| DAB molar amount | 0.166 | 0.166 | 0.057 | | |
| HMDA molar amount | n.a. | n.a. | 0.097 | | |
| Ratio TPA/Diamine | 1.006 | 1.033 | 0.996 | 1.000 | 1.012 |
| Tm salt (° C.) | 291 | 286 | 294 | 291 | 288 |
| ΔHm (J/g) | 600 | 512 | 538 | 639 | 532 |
| Weight loss (mass %) in polymerization experiments | 15.4 | | | 14.8 | |
| Theoretical weight loss (mass %) | 14.2 | 14.2 | 13.3 | 14.2 | 13.3 |
| Tm polymer (° C.) | 431 | 430 | 336 | 430 | 335 |

The results in table 1 were measured as described below.
Determination of melting temperature (Tm) of both the salt as well as the polymer, and melting enthalpy (ΔHm) by DSC method The thermal behaviour and characteristics such as melting temperature and melting enthalpy of the salts, the residual melting enthalpy of intermediate products and the melting temperature of the polymers were studied by conventional differential scanning calorimetry (DSC) applying the method according to ISO 11357-3 (2009). The measurement of residual melting enthalpy was used as an internal control for the conversion of the reaction of the salts and transformation into polyamide (pre)polymer.

For the measurements a standard heat flux Mettler DSC 823 was used and the following conditions applied. Samples of approximately 3 to 10 mg mass were weighed with a precision balance and encapsulated in (crimped) 40 μl aluminium crucibles of known mass. The aluminium crucible was sealed with a perforated aluminium crucible lid. The perforation was mechanically performed and consisted of a hole width of 50 μm. An identical empty crucible was used as a reference. Nitrogen was purged at a rate of 50 ml min−1. Heating-cooling-heating cycles with scan rates of 20° C./min, in the range of 0 to 380° C. were applied for determining the parameters that numerically characterize the thermal behaviour of the investigated materials (both salts as polymers). For the melting temperature and the residual melting enthalpy of the salts and polymers the melting peak in the first heating cycle was used.

The invention claimed is:
1. A process for preparing a salt from diamine and dicarboxylic acid, the process comprising contacting a diamine gas, having a gas temperature T-gas, with a dicarboxylic acid, thereby forming a reaction mixture comprising diamine/dicarboxylic acid salt, wherein the dicarboxylic acid and the reaction mixture are kept at a temperature T-mixture of at least 10° C. below the lowest of the melting temperature of the dicarboxylic acid (Tm-acid) and the melting temperature of the resulting diamine/dicarboxylic acid salt (Tm-salt).

2. The process according to claim 1, wherein the dicarboxylic acid is provided as a powder, as granules of granulated powder or as pellets of compressed powder, or as a mixture thereof.

3. The process according to claim 1, wherein the contacting is carried out under an absolute pressure of at most 5 bar.

4. The process according to claim 1, wherein T-mixture is at least 20° C. below the lower of Tm-acid and Tm-salt.

5. The process according to claim 1, wherein T-gas is at least 5° C. above T-mixture.

6. The process according to claim 1, wherein the contacting is carried out in an agitated bed reactor.

7. The process according to claim 1, wherein T-gas is below T-mixture plus 5° C.

8. The process according to claim 7, wherein the contacting is carried out in a static bed reactor or a moving bed reactor.

9. The process according to claim 1, wherein the dicarboxylic acid comprises an aliphatic dicarboxylic acid, or an aromatic dicarboxylic acid, or a mixture thereof.

10. The process according to claim 9, wherein the dicarboxylic acid comprises at least 50 mole %, relative to the total molar amount of dicarboxylic acid, of at least one aromatic dicarboxylic acid selected from the group consisting of terephthalic acid, 2,6-naphthalene dicarboxylic acid and biphenyl-4,4'-dicarboxylic acid.

11. The process according to claim 9, wherein the dicarboxylic acid consists of at least 95 mole % of terephthalic acid, relative to the total molar amount of dicarboxylic acid.

12. The process according to claim 10, wherein T-mixture is kept below 210° C.

13. The process according to claim 1, wherein the diamine is selected from the group consisting of aliphatic C2-C12 diamines, an aliphatic aromatic diamines, and mixtures thereof.

14. The process according to claim 13, wherein the aliphatic diamine is a linear aliphatic diamine, a trans-1,4-diaminocyclohexane, or a mixture thereof.

15. A process for preparing a semi-crystalline polyamide from diamine and dicarboxylic acid comprising:
(i) contacting a diamine gas, having a gas temperature T-gas, with a dicarboxylic acid, thereby forming a reaction mixture comprising diamine/dicarboxylic acid salt (DD-salt), wherein the dicarboxylic acid and the reaction mixture are kept at a temperature T-mixture of at least 10° C. below the lowest of the melting temperature of the dicarboxylic acid (Tm-acid) and the melting temperature of the resulting diamine/ dicarboxylic acid salt (Tm-salt); and
(ii) solid-state polymerizing the DD-salt thereby obtaining the semi-crystalline polyamide.

16. The process according to claim 15, wherein
the semi-crystalline polyamide is a semi-crystalline semi-aromatic polyamide;
the diamine comprises at 90 mole %, relative to the total molar amount of diamine, of a linear aliphatic C2-C10 diamine, an aliphatic-aromatic diamine or a mixture thereof; and
the dicarboxylic acid comprises at least 50 mole %, relative to the total molar amount of dicarboxylic acid, of at least one aromatic dicarboxylic acid selected from the group consisting of terephthalic acid, 2,6-naphthalene dicarboxylic acid, and biphenyl-4,4'-dicarboxylic acid.

17. The process according to claim 15, wherein the solid state polymerisation is at least partly carried out at a temperature above 220° C.

18. The process according to claim 16, wherein the dicarboxylic acid consists of at least 95 mole %, relative to the total molar amount of dicarboxylic acid, of at least one aromatic dicarboxylic acid selected from the group consisting of terephthalic acid, 2,6-naphthalene dicarboxylic acid and biphenyl-4,4'-dicarboxylic acid.

19. The process according to claim 18, wherein step (i) is practiced by maintaining T-mixture below 210° C. and adding the diamine in an amount such that the diamine/dicarboxylic acid molar ratio in the DD-salt obtained from step (i) is in a range of 0.75-1.10.

20. The process according to claim 18, wherein T mixture in step (i) is above 210° C.

21. The process according to claim 15, wherein the solid-state polymerization of step (ii) is carried out in a static bed reactor, a moving bed reactor, or an agitated bed reactor.

22. The process according to claim 20, wherein T-mixture is above 220° C.

23. The process according to claim 15, wherein the diamine is added in such an amount that the diamine/dicarboxylic acid molar ratio in the DD-salt obtained from step (i) is in the range of 0.90-1.10.

24. The process according to claim 1, wherein the contacting is carried out under an absolute pressure of at most 3 bar.

25. The process according to claim 1, wherein the contacting is carried out under an absolute pressure of at most 1 bar.

* * * * *